United States Patent [19]

Yasue

[11] Patent Number: 4,903,693
[45] Date of Patent: Feb. 27, 1990

[54] XENON INHALATION APPARATUS

[75] Inventor: Naoto Yasue, Yokohama, Japan

[73] Assignee: Anzai Sogyo Co., Ltd., Tokyo, Japan

[21] Appl. No.: 379,716

[22] Filed: Jul. 14, 1989

Related U.S. Application Data

[63] Continuation of Ser. No. 125,459, Nov. 24, 1987, abandoned.

Foreign Application Priority Data

Aug. 19, 1987 [JP] Japan .................. 62-204266

[51] Int. Cl.$^4$ ............................. A61M 15/00
[52] U.S. Cl. .................. 128/203.12; 128/204.18; 128/205.14; 128/716; 128/728; 128/654
[58] Field of Search .............. 128/203.12, 203.14, 128/203.25, 203.28, 204.18, 205.14, 716, 719, 725, 728, 205.21, 654; 378/53

[56] References Cited

U.S. PATENT DOCUMENTS

| | | | |
|---|---|---|---|
| 2,574,028 | 11/1951 | Fields et al. | 128/205.21 |
| 3,122,632 | 2/1964 | Quiram | 378/53 |
| 3,881,463 | 5/1975 | LeMon | 128/654 |
| 3,932,066 | 1/1976 | Eyrick et al. | 128/205.16 |
| 4,169,465 | 10/1979 | Walls et al. | 128/719 |
| 4,202,345 | 5/1980 | Farella et al. | 128/654 |
| 4,622,976 | 11/1986 | Timpe et al. | 128/654 |

Primary Examiner—Edgar S. Burr
Assistant Examiner—Aaron J. Lewis
Attorney, Agent, or Firm—Wenderoth, Lind & Ponack

[57] ABSTRACT

A xenon inhalation apparatus for introducing a mixed gas of xenon and oxygen into the lungs of a patient includes a respiration face mask, bellows having exhalation and inhalation ports, storing the mixed gas therein, and capable of varying its volume depending on the volume of the mixed gas stored therein, gas volume managing means, a series of conduit means for connecting the mask and the bellows, carbon dioxide removing means for removing carbon dioxide from exhalation gas in a closed loop system formed by the conduit means, gas flow rate control means, xenon concentration detecting means, xenon-supplying means, oxygen-supplying means, a controller for controlling the xenon-supplying means, oxygen-supplying means, electromagnetic valves and gas volume managing means, and an operation panel capable of at least setting the volume of the mixed gas stored in the bellows and the concentrations of xenon and oxygen to their respective optional values.

11 Claims, 7 Drawing Sheets

XENON INHALATION APPARATUS

This application is a division of now abandoned application, Ser. No. 07/125,459 filed on Nov. 24, 1987 now abandoned

BACKGROUND OF THE INVENTION AND RELATED ART STATEMENT

The present invention relates to a xenon inhalation apparatus capable of functionally and safely conducting a cycle beginning from the administration of xenon and terminating in the recovery of the xenon relative to a patient particularly subjected to measurement of cerebral blood flow rate or inspection of lung function.

A prior art xenon inhalation apparatus has adopted a flexible bag having a mixed gas of xenon and oxygen stored therein, management of the mixed gas on the basis of gas concentration only, a reserve bag and a lot of one-way valves as disclosed in U.S. Pat. No. 4,622,976.

In the prior art xenon inhalation apparatus, since a mixed gas of xenon and oxygen is stored in the flexible bag and managed on the basis of gas concentration only, there is a fair possibility of consuming expensive xenon in an amount more than is necessary and preparing a mixed gas in an amount more than is necessary and, in addition, precision in measurement is not so good. Further, since there are used a reserve bag, lots of one-way valves and an indoor air respiration peep valve, respiration resistance becomes large. Furthermore, since a high-pressure gas cylinder is used as a xenon supply source, the prior xenon inhalation apparatus is subjected to restrictions under the High-Pressure Gas Control Act, such as requirements of registering use of a high-pressure gas container and the name of a person responsible for handling high-pressure gas at the competent office, and handling of the high-pressure gas container must rely on the responsible person or must be conducted by those skilled in the art under the supervision of the responsible person.

OBJECT AND SUMMARY OF THE INVENTION

The present invention has been accomplished in view of the aforementioned drawbacks.

The main object of the present invention is to provide a xenon inhalation apparatus using bellows capable of varying its volume for the gas to be stored therein to thereby manage the gas on the basis of both gas volume and gas concentration, avoid wasteful consumption of expensive xenon in preparing a mixed gas and adding xenon and recover the xenon and also using a blower to thereby administer a mixed gas of high precision to a patient without using one-way valves under the same circumstances as those obtained by the use of one-way valves.

To attain the object described above, according to the present invention, there is provided a xenon inhalation apparatus for introducing a mixed gas of xenon and oxygen into the lungs of a patient, comprising a respiration face mask through which the mixed gas is introduced into the lungs, bellows having an exhalation port and an inhalation port, storing the mixed gas therein, and capable of varying its volume depending on the volume of the mixed gas stored in the bellows, a series of conduit means for connecting the respiration face mask, exhalation port and inhalation port so as to communicate with one another, carbon dioxide removing means for removing carbon dioxide, when the series of conduit means form a closed loop system, from exhalation in the closed loop system, gas flow rate control means for controlling the flow rate of the mixed gas in exhalation and inhalation tubes connected to the respiration face mask through a conduit, xenon concentration detecting means for detecting the concentration of xenon flowing into the respiration face mask, xenon-supplying means for supplying xenon into the bellows, oxygen-supplying means for supplying oxygen into the bellows, a controller for controlling the xenon-supplying means, oxygen-supplying means, electromagnetic valves mounted on the series of conduit means and mounted on conduits in a sampling system, and gas volume managing means, and an operation panel capable of at least setting the volume of the mixed gas stored in the bellows and the concentrations of xenon and oxygen to respective optional values.

The above and other objects, characteristic features and advantages of the present invention will become more apparent to those skilled in the art as the disclosure is made in the following description of a preferred embodiment of the invention, as illustrated in the accompanying drawings.

DETAILED DESCRIPTION OF THE PREFERRED EMBODIMENT

Figure 1:
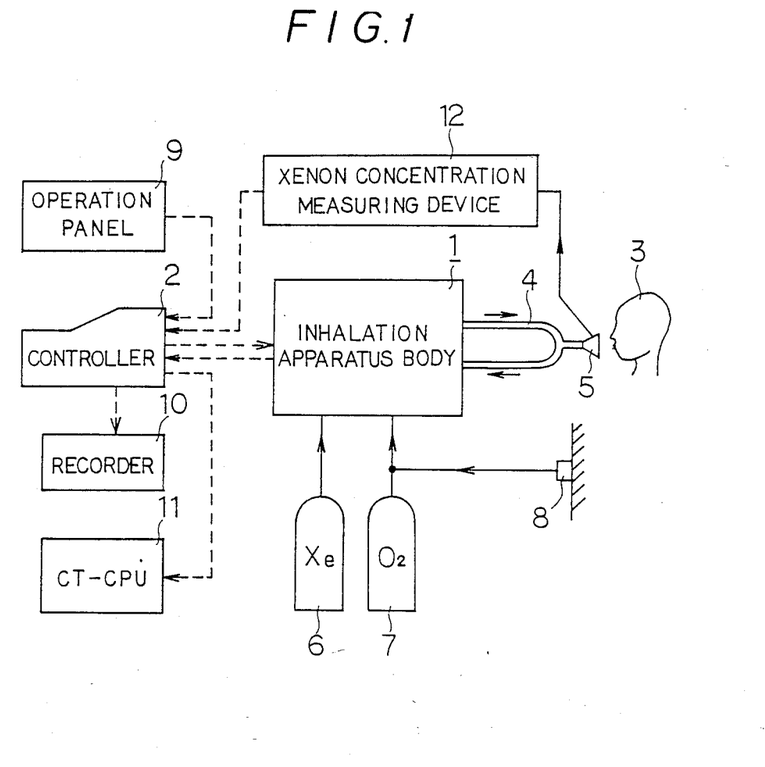
FIG. 1 is a schematic block diagram illustrating one embodiment of the xenon inhalation apparatus according to the present invention.
Figure 2:
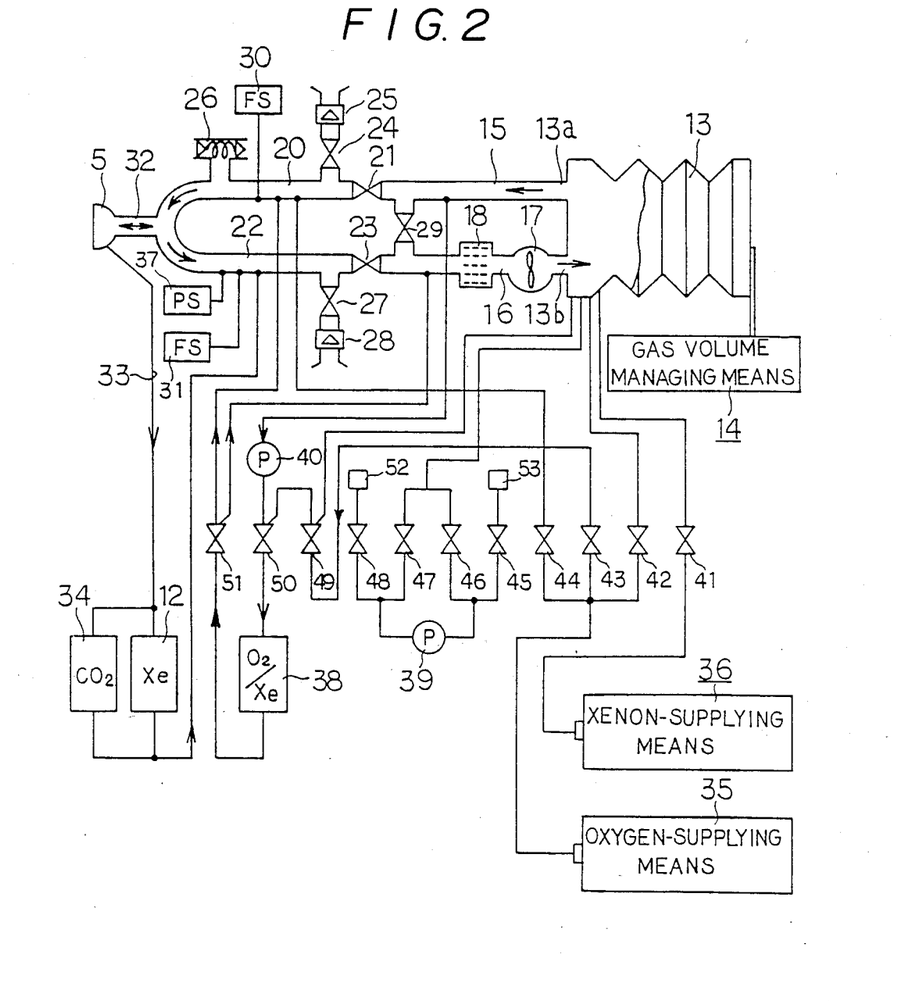
FIG. 2 is a schematic view illustrating the construction of the embodiment.

The present invention will now be described with reference to the illustrated embodiment. FIG. 1 is a block diagram illustrating one embodiment of the xenon inhalation apparatus according to the present invention, and FIG. 2 is a partially omitted schematic view illustrating the apparatus of FIG. 1.

As shown in FIG. 1, the xenon inhalation apparatus roughly comprises an inhalation apparatus body 1 and a controller 2. To the inhalation apparatus body 1 is connected to a conduit 4 for supplying a mixed gas of preset concentration to a patient 3. The conduit 4 is provided with a respiration face mask 5 for the patient 3. The inhalation apparatus body 1 is fitted with a xenon cylinder 6 and an oxygen cylinder 7 serving as sources for xenon and oxygen which constitute the aforementioned mixed gas and also with an indoor oxygen-supplying port 8 serving to supply oxygen from an indoor oxygen-supplying source provided outside the inhalation apparatus body 1.

The controller 2 is provided with an operation panel 9 and receives a command outputted from the operation panel 9, thereby controlling the inhalation apparatus body 1, the opening and closing of electromagnetic valves (not shown) for the xenon cylinder 6, oxygen cylinder 7, conduit 4, etc. To the controller 2 is connected a recorder 10 for recording the concentrations of xenon and oxygen in the aforementioned mixed gas, etc. automatically. The controller 2 outputs therefrom data on xenon and carbon dioxide contained in the gas exhaled by the patient 3. The data are inputted to a central processing unit (CPU) 11 utilizing the computed tomography (CT). Of these data, particularly, those on the xenon concentration can be used as fundamental data which is very important in measuring/computing the cerebral blood flow rate and can serve as a factor important in analyzing the condition of a disease. For this reason, a xenon concentration measuring device 12 for measuring the concentration of xenon contained in the gas exhaled by the patient 3 is required to have high precision. The xenon inhalation apparatus in this embodiment adopts as the xenon concentration measuring device 12 a xenon concentration measuring apparatus which is excellent in speed of response and precision of measurement and making use of radiation.

Figure 8:
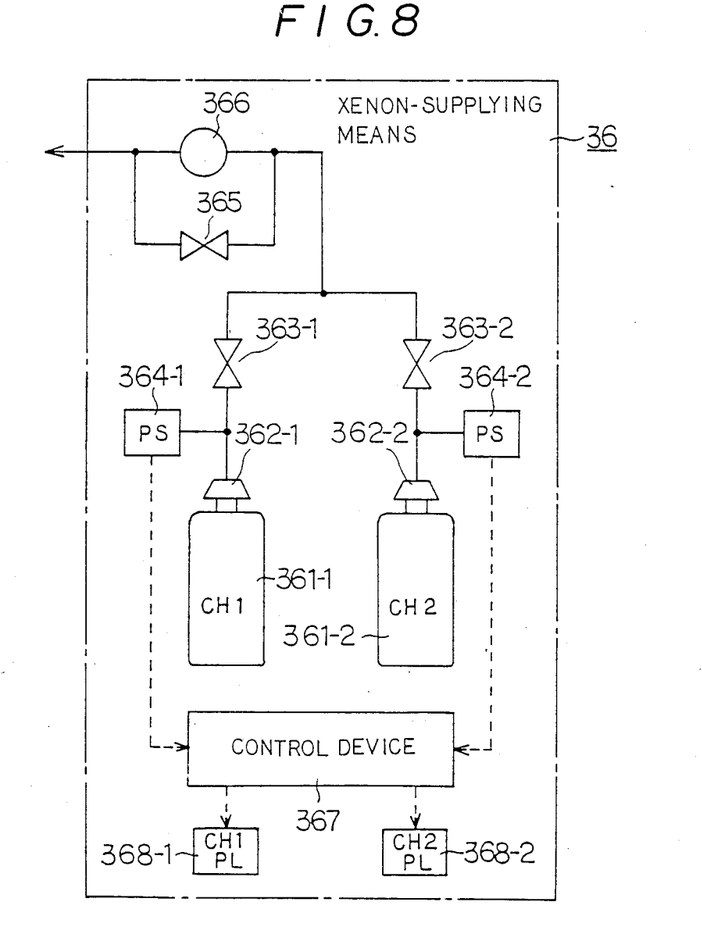
FIG. 8 is a schematic view illustrating the construction of xenon-supplying means having low-pressure gas cylinders.

The solid lines and phantom lines in FIG. 1 and FIG. 8 designate flow passages for gases and electric signals, respectively.

In FIG. 2, reference numeral 13 designates a bellows of an accordion structure capable of elongation and contraction. The bellows 13 is provided at one end thereof with an exhalation port 13a and an inhalation port 13b and at the other end (free end) thereof with gas volume managing means 14 which detects the position at which the free end of the bellows 13 has moved to measure and determine the volume of the gas contained in the bellows 13.

Figure 4:
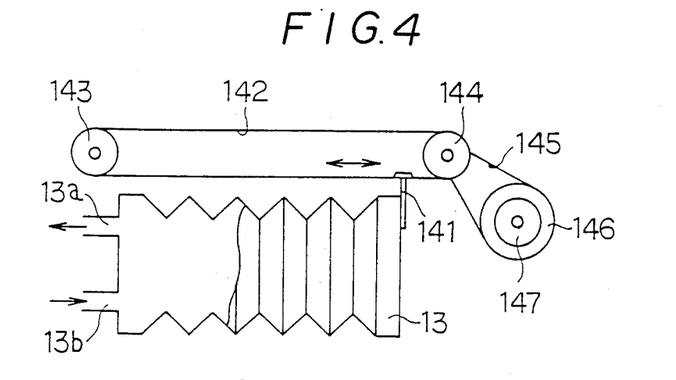
FIG. 4 is a schematic view illustrating the construction of gas volume managing means used in the embodiment.

As illustrated in FIG. 4, the gas volume managing means 14 is connected to the bellows 13 by a connecting member 141 which is fixed to part of an endless chain 142 stretched between a pair of rotary gears 143 and 144. Rotation of the rotary gear 144 is transmitted to a rotary pulley 146 through an endless belt 145 stretched between the central shaft of the rotary gear 144 and the rotary pulley 146. About the central shaft of the rotary pulley 146 there is coaxially fitted a potentiometer 147. With this construction, therefore, the amount of the lateral movement of the free end of the bellows 13 based on the elongation or contraction thereof is converted into the number of revolutions of the potentiometer 147 via the connecting member 141, endless chain 142, rotary gear 144, endless belt 145 and rotary pulley 146, and the amount of the gas contained in the bellows 13 corresponding to the elongation or contraction of the bellows 13 can be expressed in terms of the value of resistance of the potentiometer 147. In this embodiment, since the endless chain 142 is used, the amount of the lateral movement of the bellows 13 based on the elongation or contraction thereof can be transmitted without being varied to the rotary gear 144, and the rotation of the rotary gear 144 is transmitted via the endless belt 145 to the rotary pulley 146 coaxial with the potentiometer 147. The potentiometer 147 may optionally be fitted about the central shaft of the rotary gear 144. However, in order to determine the number of revolutions of the potentiometer 147 more freely and obtain a higher degree of freedom in revolution, the potentiometer 147 is preferably fitted about the central shaft of the rotary pulley 146 as in this embodiment.

Figure 3:
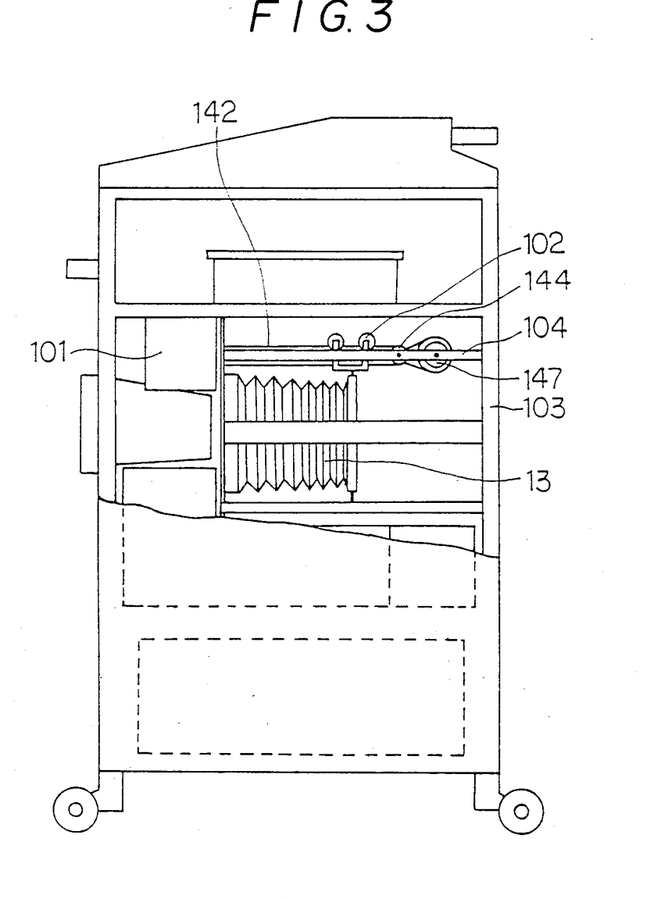
FIG. 3 is a partially cutaway side view illustrating a housing for accommodating the xenon inhalation apparatus shown in FIG. 1.

The rotary gear 143 is accommodated within a gear box 101 shown in FIG. 3 which is a partially cutaway side view illustrating a housing for accommodating the xenon inhalation apparatus therein. On the free end side of the bellows 13 there are provided pinions 102 rotatably mounted by means of bearings or the like and guided along a rail 104 mounted on a frame 103, and the free end of the bellows 13 can freely be moved by a balance spring (not shown) or a like member. With this construction, therefore, the bellows 13 can elongate or contract, with little resistance, in accordance with the respiration of the patient 3.

Returning to FIG. 2, conduits 15 and 16 are connected to the exhalation and inhalation ports 13a and 13b respectively. Midway along the length of the conduit 16 there are provided a blower 17 for circulating the mixed gas in the bellows 13 at a suitable flow speed and carbon dioxide removing means 18 such as soda lime which absorbs carbon dioxide. An inhalation tube 20 and an exhalation tube 22 which communicate with the respiration face mask 5 through a respiration tube 32 are connected to the aforementioned conduits 15 and 16 by means of electromagnetic valves 21 and 23, respectively. To the inhalation tube 20 is connected a one-way valve 25 by means of an electromagnetic valve 24. The one-way valve 25 is adapted to introduce the indoor air into the inhalation tube therethrough. The inhalation tube 20 is provided with a safety valve 26 actuated, when the internal pressure of the inhalation tube 20 is less than a prescribed pressure, to introduce the indoor air into the inhalation tube 20 and, when the internal pressure is more than the prescribed pressure, to relieve the interior of the inhalation tube 20. On the other hand, to the exhalation tube 22 is connected a one-way valve 28 by means of an electromagnetic valve 27. The one-way valve 28 is adapted to discharge the gas from the exhalation tube 22 to the indoor air therethrough. In a conduit between the conduit 15 connecting the electromagnetic valve 21 and the exhalation port 13a of the bellows 13 and the conduit 16 connnecting the electromagnetic valve 23 and the inhalation port 13b of the bellows 13, there is provided an electromagnetic valve 29. By suitably opening and closing a series of these electromagnetic valves 21, 23, 24, 27 and 29, there is formed a completely or partially closed loop system for the flowing of gas, which will later be described in detail.

The inhalation and exhalation tubes 20 and 22 are provided with flow rate sensors 30 and 31, respectively, by which the speed of revolution of the blower 17 is controlled to maintain the flow rate of the gas within the inhalation and exhalation tubes 20 and 22 within a given range at all times. The mixed gas stored within the bellows 13 is circulated by the blower 17 in a closed loop system comprising the bellows 13, conduit 15, inhalation tube 20, exhalation tube 22 and conduit 16. Therefore, the patient 3 inhales the circulating mixed gas through the respiration tube 32 and respiration face mask 5, whereas the exhalation gas from the lungs of the patient 3 is discharged into the exhalation tube 22 through the respiration face mask 5 and respiration tube 32 by the gas flow pressure controlled by the blower 17 without being discharged into the inhalation tube 20. That is to say, the exhalation and inhalation are distinguished from each other by the gas flow pressure alone controlled by the blower 17 without providing, at portions of the inhalation and exhalation tubes 20 and 22 in the vicinity of the respiration face mask 5 respectively, mechanical one-way valves for preventing the gas from counterflow, thereby establishing a good state of the patient's respiration. The gas flow rate required for establishing a good respiration state with the aforementioned gas flow pressure alone falls in the range of 20 to 40 l/min. The speed of revolution of the blower 17 is controlled by the flow rate sensors 30 and 31 to maintain the gas flow rate within that range. It goes without saying that the flow rate sensors 30 and 31 may be omitted if the blower 17 has a function to always maintain the gas flow rate in the range of 20 to 40 l/min.

The respiration face mask 5 is provided with a tube 33 for selectively passing therethrough the gas exhaled by the patient 3. The concentrations of xenon and carbon dioxide in the patient's exhalation gas passing through the tube 33 are measured by a xenon concentration measuring device 12 and a carbon dioxide concentration measuring device 34, respectively. As the carbon dioxide concentration measuring device 34, a gas concentration measuring device available on the market can be used. However, the xenon concentration measuring device 12 is required to be excellent in speed of response and precision of measurement for the concentration of xenon in the exhalation gas about the patient's mouth because the concentration of xenon in the gas finally exhaled by the patient into the respiration face mask 5 is in proportion to the concentration of xenon in the arterial blood and also because the xenon concentration of the arterial blood is an important factor for calculating the cerebral blood flow rate. There have been available on the market heat transfer type xenon concentration measuring devices and those utilizing a mass spectrometer. However, the former is inferior in speed of response and precision of measurement and the latter requires much time to measure the xenon concentration in spite of superior precision of measurement. For this reason, the commercially available xenon concentration measuring devices cannot practically be used in the xenon gas inhalation apparatus of the present invention. In the present invention, therefore, a xenon concentration measuring device which is superior in speed of response and precision of measurement and which utilizes radiation is used as illustrated in FIG. 5.

Figure 5:
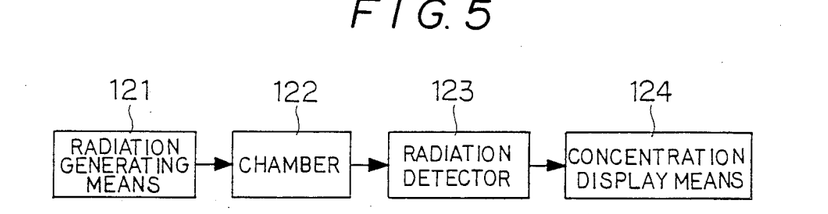
FIG. 5 is a schematic block diagram illustrating a xenon concentration gauge utilizing radiation.
Figure 6:
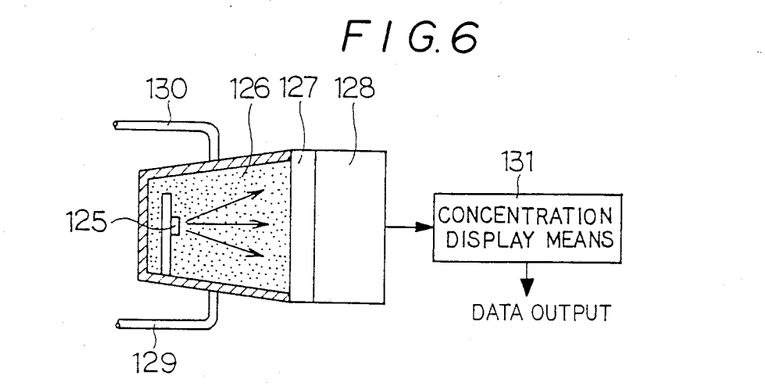
FIG. 6 is a schematic view illustrating the construction of a xenon concentration measuring device utilizing X-rays.
Figure 7:
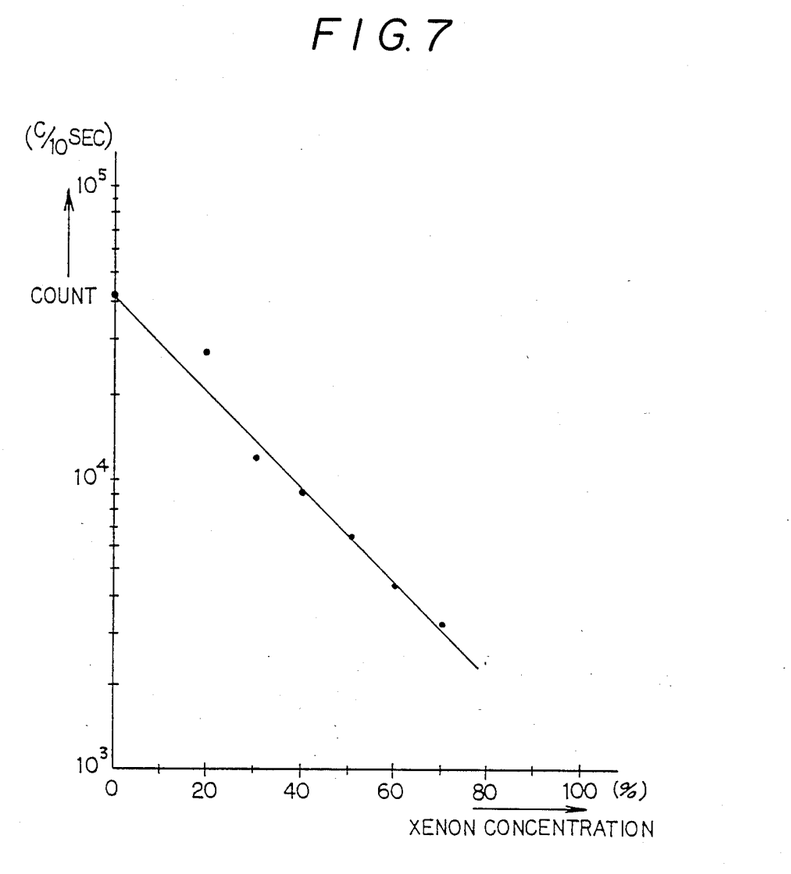
FIG. 7 is a graph illustrating the relation between the radiation count and the concentration of xenon obtained by experiments using the xenon concentration measuring device of FIG. 6.

FIG. 5 is a schematic view illustrating the aforementioned xenon concentration measuring device, FIG. 6 is a schematic view illustrating a xenon concentration measuring device utilizing X-rays, and FIG. 7 is a graph illustrating the results of experiments using the device of FIG. 6 to obtain the relation between the xenon concentration and the radiation count.

In FIG. 5, reference numeral 121 designates a radiation generating means, numeral 122 designates a chamber, numeral 123 designates a radiation detector, and numeral 124 designates a concentration display means. The chamber 122 is filled with exhalation gas to be subjected to measurement. Radiation exclusive of $\alpha$-rays (i.e. X-rays, $\gamma$-rays or $\beta$-rays) emitted from the radiation generating means 121 disposed on one side of the chamber 122 is introduced into the chamber 122 to pass through the exhalation gas within the chamber 122. The radiation generating means 121 may be either a radiation generator or a radioactive substance. The radiation detector 123 is disposed on the other side of the chamber 122 at a prescribed distance from the radiation generating means 121. Therefore, the radiation exclusive of $\alpha$-rays which has emitted from the radiation generating means 121 passes through the chamber 122 and reaches the radiation detector 123. The radiation detector 123 may suitably be selected depending on the kind of radiation emitted from the radiation generating means 121, such as from combinations of a gas, liquid or solid scintillator and a photomultiplier tube, ionization chamber, proportional counter tube or Geiger-Müeller counter, for example. The radiation emitted from the radiation generating means 121 toward the gas under measurement introduced into the chamber 122 collides against the molecules of the gas and is absorbed and diffused by the molecules, with the result that part of the radiation cannot reach the radiation detector 123. The ratio of the radiation incapable of reaching the radiation detector 123 to the radiation capable of reaching the radiation detector 123 depends on the concentration of the gas under measurement introduced in the chamber 122. Therefore, the concentration of the gas under measurement present within the chamber 122 can be measured by taking count of the radiation detected by the radiation detector 123 with the concentration display means 124.

An example of a gas concentration measuring device utilyzing X-rays or $\gamma$-rays (hereinafter referred to collectively as X-rays) will be described with reference to FIG. 6. in FIG. 6, reference numeral 125 designates an X-ray source, numeral 126 designates a chamber, numeral 127 designates a scintillator formed of sodium iodide (NaI), for example, numeral 128 designates a photomultiplier tube, numeral 129 designates a gas flow inlet pipe, numeral 130 designates a gas flow outlet pipe, and numeral 131 designates a concentration display means. The X-ray source 125 is disposed within the chamber 126 so as to face the scintillator 127. X-rays emitted from the X-ray source 125 reach the scintillator 127 while being absorbed and diffused by the gas present within the chamber 126 as an object to be measured.

When X-rays pass through a substance, they are attenuated by the substance. The ratio of the attenuation is determined by the energy of the X-rays and the mass of the substance through which the X-rays pass. In general, when X-rays having energy E advance a distance of d cm within a gas, the intensity I of the X-rays at the position of the distance of d cm is represented by the formula: $I = I_0 e^{-\mu d}$ wherein $I_0$ stands for the initial intensity of the X-rays, e for the base of natural logarithms, and $\mu$ for the attenuation coefficient. Therefore, the ratio of the X-rays attenuated during the distance of d cm by the gas is represented by the formula: $1 - I/I_0$. The attenuation ratio is determined by the substance constituting a gas. In the case of a mixed gas composed of known gas components, therefore, the concentration of any one of the gas components can be measured from the number N of the photons attenuated by the gas component. In the case of X-rays, the lower the energy E of the X-rays, the higher the attenuation ratio. Now, assuming that the energy of X-rays is E and that the atomic number of a substance constituting a gas is Z, when the energy E of the X-rays is low, the attenuation of the X-rays will result from the photoelectric effect and the attenuation ratio is in proportion to the fifth power of the atomic number Z and in inverse proportion to 7/2 of the energy E of the X-rays. Therefore, when the gas components constituting a mixed gas, such as of xenon and oxygen, have atomic numbers, one larger than the other by a given number, X-rays will act more on the gas component having the smaller atomic number. For this reason, the concentration of the gas component having the larger atomic number in the mixed gas can be measured.

The X-ray source 125 emits X-rays at all times and, when the gas composed of gas components of different atomic numbers and introduced into the chamber 126 has constant concentration, for example, a constant number of photons corresponding to the constant gas concentration reach the scintillator 127 disposed at a distance of d cm from the X-ray source 125 so as to face the X-ray source 125. However, since the X-ray source 125 emits X-rays at random, there gives rise to statistical fluctuation, the value of which is in inverse proportion to $\sqrt{N_0}$. The photons which have reached the scintillator 127 are converted into light beams of long wavelengths at that place. The light beams are converted into electric signals at the photomultiplier tube 128, and the electric signals are suitably amplified by a charge sensitive amplifier or linear amplifier, for example, and are inputted to a counting circuit. As a result, the photons which have reached the scintillator 127 are counted one by one.

When the gas under measurement present within the chamber 126 is composed of xenon Xe and oxygen $O_2$, since the atomic number of xenon is much larger than that of oxygen, the ratio of X-rays being attenuated by the photoelectric effect becomes much higher when the X-rays pass through xenon than when the X-rays pass through oxygen. Further, the higher the concentration of xenon in the gas under measurement, the higher the ratio of the X-rays being attenuated and the lower the number of photos reaching the scintillator 127. In other words, the concentration of xenon in the gas present within the chamber 126 is in inverse proportion to the electric signals outputted from the photomultiplier tube 128. While this inverse proportion relationship is utilized, the electric signals are subjected to suitable signal processing and displayed as xenon concentration on the concentration display means 131 which outputs the displayed xenon concentration data.

FIG. 7 shows the number of X-rays (photons) counted for about 10 seconds by a counting circuit within the concentration display means 131 under the conditions that the gas within the chamber 126 is composed of xenon and oxygen, that a radioactive substance Fe-55 is used as the X-ray source 125 capable of emitting X-rays of about 25 $\mu$Ci, that the distance d between the X-ray source 125 and the scintillator 127 is set to be about 1.3 cm, and that the concentration of xenon in the gas varies. As is clear from FIG. 7, the count varies depending on the xenon concentration and, more specifically, the higher the xenon concentration, the less the number of the photons reaching the scintillator 127.

Thus, the gas concentration measuring device using radiation, adopted as the xenon concentration measuring device 12 of the present invention is excellent in speed of response and precision of measurement and, therefore, can precisely measure the concentration of xenon in the gas finally exhaled by the patient.

Returning again to FIG. 2, oxygen and xenon are supplied from oxygen-supplying means 35 and xenon-supplying means 36 respectively into the bellows 13. As shown in FIG. 1, oxygen is supplied via a pressure-reducing valve (not shown) either from the oxygen cylinder 7 or from the indoor oxygen-supplying port 8 serving as an indoor oxygen-supplying source disposed outside the xenon inhalation apparatus. The xenon-supplying means 36 will be described in detail with reference to FIG. 8. It has a dual-channel construction. A first channel comprises a disposable xenon cylinder 361-1, a gas outlet 362-1, an electromagnetic valve 363-1 and a pressure sensor 364-1. A second channel comprises a disposable xenon cylinder 361-2, a gas outlet 362-2, an electromagnetic valve 363-2 and a pressure sensor 364-2. Xenon discharged out of the gas outlet 362-1 mounted on the xenon cylinder 361-1 flows into a pressure reducer 366 through the electromagnetic valve 363-1 and is reduced in pressure to a prescribed value, e.g. 1.2 kg/cm$^2$, by the pressure reducer 366 and then discharged out of the xenon-supplying means 36. When the amount of xenon in the xenon cylinder 361-1 is decreased and the aforementioned prescribed pressure is detected by the pressure sensor 364-1, a control device 367 outputs a control signal for opening an electromagnetic valve 365. As a result, the xenon discharged from the xenon cylinder 361-1 is discharged out of the xenon-supplying means 36 through the electromagnetic valve 365 without passing through the pressure reducer 366. When the pressure sensor 364-1 detects that the xenon cylinder 361-1 has been emptied, the control device 367 immediately causes the electromagnetic valve 363-2 of the second channel to be opened, thereby switching the xenon-supplying source from the empty xenon cylinder 361-1 to the filled xenon cylinder 361-2. At this time, the electromagnetic valve 365 is closed, and xenon discharge out of the xenon cylinder 361-2 is reduced in pressure to the prescribed value, e.g. 1.2 kg/cm$^2$, by the pressure reducer 366 and then discharged out of the xenon-supplying means 36. The empty xenon cylinder 361-1 of the first channel is interchanged with a filled xenon cylinder which is ready for use when the xenon cylinder 361-2 of the second channel has been emptied. The control device 367 is associated with the xenon cylinder supplying xenon and is programmed to remember which xenon cylinder is supplying xenon. Therefore, when it is required to newly supply xenon from the xenon-supplying means 36, the xenon cylinder memorized by the control device 367 is preferentially used until it is completely emptied. The control device 367 also serves to light either a pilot lamp 368-1 associated with xenon cylinder 361-1 of the first channel or a pilot lamp 368-2 associated with the xenon cylinder 361-2 of the second channel so as to show which of the xenon cylinders 361-1 and 361-2 is now supplying xenon. Thus, the xenon cylinder supplying xenon is preferentially used until it is completely emptied, and the apparatus is then switched to a filled xenon cylinder. Therefore, expensive xenon can effectively be used economically.

Figure 9:
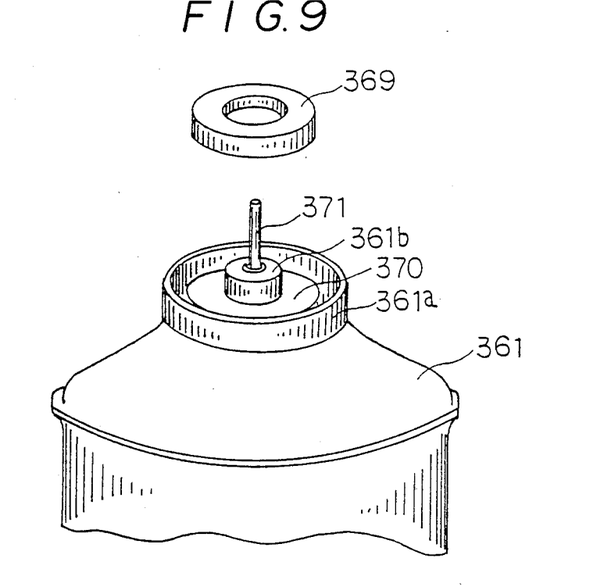
FIG. 9 is an explanatory view illustrating the head end portion of a low-pressure xenon cylinder usable in the present invention and distinguishable from a different low-pressure gas cylinder.

The xenon cylinders 361-1 and 361-2 used in this embodiment are disposable low-pressure gas cylinders each having an inner volume of about 7 l which can sufficiently cover the amount of gas generally consumed by a single patient, which is about 5 l. Therefore, the gas cylinder is not restricted by the regulations of the High-Pressure Gas Control Act and can be easily interchanged by anyone with a fresh gas cylinder. In order to distinguish the xenon cylinder from other gas cylinders, a safety ring 369 is fixed with an adhesive agent or by any means to an annular recess 370 between a cylinder head end portion such as a flange 361a and a nozzle holder 361b, as illustrated in FIG. 9. Therefore, the presence or absence of the safety ring 369 makes it possible to discriminate between a xenon gas cylinder and a different gas cylinder.

Figure 10:
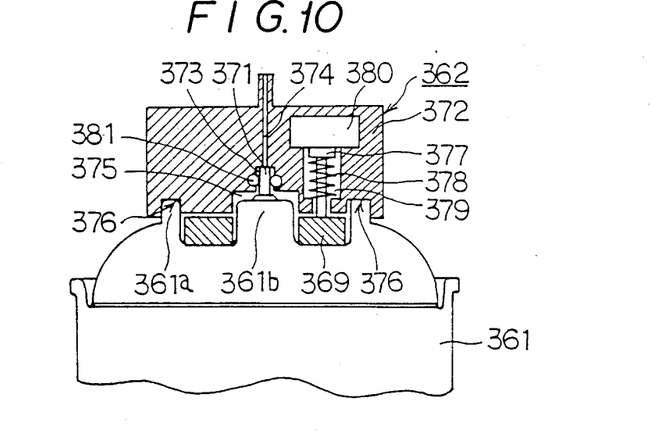
FIG. 10 is a cross-sectional view illustrating a gas outlet mounted on the low-pressure xenon cylinder.

FIG. 10 is a cross section showing a gas outlet 362 corresponding to the gas outlets 362-1 and 362-2 shown in FIG. 8. The gas outlet 362 has a gas outlet body 372 provided at the center thereof with a groove 373 for depressing the leading end of a nozzle 371 of the xenon cylinder 361, with a gas canal 374 communicating with the groove 373, and also with a recess portion 375 formed in a stepped manner relative to the groove 373 for admitting the nozzle holder 361b. The gas outlet body 372 is also provided with an annular groove 376 held concentric with the recess portion 375 for admitting the cylinder head end portion 361a of the xenon cylinder 361. A portion of the gas outlet body 372 corresponding in position to the annular recess 370 of the xenon cylinder 361 is formed with a hole 379 in which a pin 377 engaged with a spring 378 and a switch 380 actuated by the movement of the end face of the pin 377 are accommodated. When the gas outlet 362 is set in position on the xenon cylinder 361, as illustrated in FIG. 10, the safety ring 369 fixed to the annular recess 370 of the xenon cylinder 361 for distinguishing it from a different gas cylinder causes the pin 377 to be moved upwardly against the biasing force of the spring 378. As a result, the end face of the pin 377 pushes the switch 380 to be actuated. When the switch 380 has been actuated, the control device 367 shown in FIG. 8 confirms that the cylinder having the gas outlet 362 is the very xenon cylinder filled with xenon and then brings the electromagnetic valve 363-1 or 363-2 to an operable state. If the cylinder is not a xenon cylinder, since it does not have a safety ring 369, the pin 377 will not be pushed up. In this case, therefore, the switch 380 is not operated and the control device 367 does not act on the electromagnetic valve 363-1 and 363-2. Thus, it is possible to prevent a low-pressure gas cylinder similar in appearance to but different from a xenon cylinder from being used by mistake in place of a xenon cylinder. Further, in the groove 373 is fitted an O-ring which serves to press the periphery of the nozzle 371 when the nozzle 371 has been inserted into the groove 373, thereby preventing the xenon from leaking.

Returning again to FIG. 2, the exhalation tube 22 is provided with a pressure sensor 37 for detecting the internal gas pressure of the exhalation tube, and a xenon/oxygen concentration measuring device 38 used for setting the concentration of xenon in the mixed gas within the bellows 13 at a prescribed value in associated with the conduit 15. Since the xenon/oxygen concentration measuring device 38 aims at controlling the concentration of xenon in the mixed gas within the bellows 13, it is not required to have such excellence in speed of response and precision of measurement as in the case of the xenon concentration measuring device 12 shown in FIG. 1. A commercially available heat transfer type measuring device inferior in speed of response and precision of measurement to the xenon concentration measuring device 12 can be used as the xenon/oxygen concentration measuring device 38. Further, reference numerals 39 and 40 designate pumps, and numerals 41 to 51 electromagnetic valves which are controlled by the controller 2 shown in FIG. 1. Denoted by numerals 52 and 53 are a discharge port and an inlet port, respectively, which will be described later.

The operation panel 9 shown in FIG. 1 can optionally set at least the amount of the gas stored in the bellows 13, the concentration of xenon gas and the concentration of oxygen, and is provided with operation buttons etc. capable of optionally selecting a closed loop system or a partially closed loop system which will be described in detail later.

Now, how to use the xenon inhalation apparatus according to the present invention will be described.

(I) Preparation of a mixed gas of xenon and oxygen:

Prior to the preparation of a mixed gas, the gas remaining within the bellows 13 is discharged out of the discharge port 52 by closing the electromagnetic valves 21 and 23, opening the electromagnetic valve 29, and normally operating the pump 39 to cause the residual gas to flow through the electromagnetic valve 46, pump 39 and electromagnetic valve 48. As a result, the bellows 13 contracts to the fullest extent so that the gas stored in the bellows 13 becomes 0 l. During the discharge of the residual gas, the concentration of xenon in the residual gas within the bellows 13 is measured by the xenon/oxygen concentration measuring device 38 which constitutes a sampling system in conjunction with the bellows 13, pump 40, electromagnetic valves 50 and 51 and conduit 16. When the measured concentration of xenon in the residual gas is more than a prescribed value, e.g. 3%, the indoor air is introduced from the intake port 53 into the bellows 13 through the electromagnetic valve 45, pump 39 and electromagnetic valve 47 by reversely operating the pump 39 to allow the bellows 13 to elongate. When the bellows 13 has elongated to the fullest extent, the pump 39 is normally operated again to form such a residual gas discharging line as described above, thereby contracting the bellows 13. By repeating the cycle of contraction and elongation of the bellows 13 as described above, the concentration of xenon in the residual gas in the bellows 13 can be decreased to a value less than the aforementioned prescribed value. That is to say, the bellows 13 is washed out with the indoor air. Therefore, the mixed gas used in the respiration of a previous patient will not influence the preparation of a mixed gas for use in respiration of a new patient, and the concentration of xenon preset by the operation panel 9 can be precisely maintained intact.

The operation panel 9 has preset the volume of a mixed gas to be newly prepared and the concentration of each of xenon and oxygen in the mixed gas and the preset data are inputted to the controller 2. The controller 2 calculates a fundamental concentration of oxygen necessary for obtaining the concentration of oxygen corresponding to that preset by the operation panel 9 on the basis of both the aforementioned data inputted to the controller 2 and a so-called dead volume which is the total volume of the gas in the bellows 13, respiration tube 15 and 16, inhalation tube 20, exhalation tube 22, conduit 32, respiration face mask 5 and lungs of a patient in a state of the bellows 13 contracted to the fullest extent, i.e. in a 0 l state of the bellows 13. Oxygen is supplied from the oxygen-supplying means 35 into the bellows 13 until the calculated fundamental concentration of oxygen becomes equal to the oxygen concentration of the xenon/oxygen concentration measuring device 38 by opening the electromagnetic valve 42. As soon as the concentration of oxygen within the bellows 13 is coincident with the fundamental concentration of oxygen calculated by the controller 2, the electromagnetic valve 42 is closed and the electromagnetic valve 41 is then opened to supply xenon from the xenon-supplying means 36 into the bellows 13. Consequently, the bellows 13 is elongated by the oxygen and xenon supplied thereinto and, when the volume of the mixed gas within the bellows 13 has reached the volume of the gas volume preset by the gas volume managing means 14, the gas volume managing means 14 sends a signal indicating the aforementioned fact to the controller 2. As a result, the electromagnetic valve 41 is closed by the controller 2. Therefore, the bellows 13 is filled with the preset volume of mixed gas composed of xenon and oxygen in respective desired concentrations. As is clear from the above, with the gas volume managing means 14, it is possible to prepare a mixed gas in a desired volume composed of xenon and oxygen in their respective preset concentrations and to supply expensive xenon into the bellows 13 in an amount necessary for and indispensable to the preparation of the preset volume of mixed gas. Therefore, there is no fear of xenon being consumed in an amount more than is necessary.

Further, at the time the mixed gas is prepared, i.e. in a standby mode wherein the electromagnetic valves 21 and 23 have been closed and the electromagnetic valves 24 and 27 have been opened, a patient having the respiration face mask 5 attached to the mouth can inhale the indoor air through the one-way valve 25, electromagnetic valve 24, inhalation tube 20 and respiration tube 32 and can also exhale to the interior of a room through the respiration tube 32, exhalation tube 22, electromagnetic valve 27 and one-way valve 28. Therefore, the patient can acclimatize himself or herself to the state of respiration through the respiration face mask 5. When the patient is required to inhale oxygen of a high concentration, for example, the electromagnetic valve 44 is opened to introduce oxygen from the oxygen-supplying means 35 into the inhalation tube 20 through the electromagnetic valve 44. At this time, the patient inhales a mixed gas of the indoor air and the oxygen supplied from the oxygen-supplying means 35.

(II) Respiration of a patient:

When a patient inhales a mixed gas of xenon and oxygen through the respiration face mask 5, in an initial stage of washing in the lungs of the patient with a mixed gas of xenon and oxygen, the mixed gas can be supplied by utilizing either a closed loop system or a partially closed loop system. In order to effectively make the most of expensive xenon, the closed loop system is utilized at the initial stage so that the mixed gas within the bellows 13 is completely circulated without being discharged out of the system. On the other hand, in order for the patient to inhale xenon of a given concentration from his or her initial respiration, the partially closed system is utilized so that the exhalation gas of the patient is discharged out of the system until the concentration of xenon in his or her lungs becomes equal to that of the xenon in the mixed gas supplied into the lungs. Upon confirmation of the equality, the partially closed loop system is switched to the closed loop system, whereby the mixed gas within the bellows 13 is circulated within the closed loop system without being discharged out of the system.

(A) Respiration of a patient in a closed loop system:

When a command to form a closed loop system has issued from the operation panel 9, the electromagnetic valves 24, 27 and 29 are closed, whereas the electromagnetic valves 21 and 23 are opened. As a result, there is formed a closed loop system beginning from the bellows 13, passing successively through the conduit 15, electromagnetic valve 21, inhalation tube 20, exhalation tube 22, electromagnetic valve 23 and conduit 16 including the soda lime 18 and blower 17, and terminating in the bellows 13. The mixed gas of xenon and oxygen prepared within the bellows 13 is circulated in the closed loop system. The circulation of the mixed gas is carried out by the blower 17 so that the mixed gas is controlled to flow through the inhalation and exhalation tubes 20 and 22 at a flow rate of 20 to 40 l/min. When a patient respires through the respiration face mask 5 in the state of the controlled flow rate of 20 to 40 l/min., the respiration resistance can be made small and the exhalation gas of the patient can be discharged into the exhalation tube 22 without staying in the respiration tube 32. That is to say, inhalation gas and exhalation gas are distinguished from each other by the flow pressure alone of the mixed gas based on the function of the blower 17, without providing the portions of the exhalation and inhalation tubes 22 and 20 in the vicinity of the respiration tube 32 with mechanical one-way valves, to obtain substantially the same effects as those obtained in the case where such one-way valves are provided on the aforementioned portions.

When the closed loop system is used from the beginning, xenon is reduced in concentration by the exhalation gas from the lungs of the patient. However, since the xenon is not discharged out of the closed loop system, the amount of the xenon is maintained constant at all times. The expensive xenon is thus utilized effectively. The concentration of the xenon introduced into the patient through the respiration face mask 5 at the initial stage is measured by the xenon concentration measuring device 12. In view of the fact that the xenon concentration serves as fundamental data for disease condition analysis which is very important for the measurement of cerebral blood flow rate or the inspection of lung function, the xenon concentration measuring device 12 used in the present invention is of a type excellent in speed of response and precision of measurement and utilizing radiation as described in the foregoing.

(B) Respiration of a patient in a partially closed loop system:

When a command to form a partially closed loop system has issued from the operation panel 9, the electromagnetic valves 21, 24, 27 and 29 are opened, whereas the electromagnetic valve 23 is closed. Since the electromagnetic valve 23 is closed in the partially closed loop system, although there cannot be obtained the same effects as those obtained in the case where mechanical one-way valves are provided on the portions of the inhalation and exhalation tubes 20 and 22 in the vicinity of the respiration tube 32, the blower 17 applies pressure to the mixed gas flowing into the conduit 15. For this reason, when the patient inhales through the respiration face mask 5, the mixed gas within the bellows 13 passes successively through the conduit 15, electromagnetic valve 21, inhalation tube 20 and respiration tube 32 into the mouth of the patient. At this time, the indoor atmospheric pressure acts to contract the bellows 13 by an extent corresponding to the amount of the mixed gas inhaled by the patient and, therefore, the patient can inhale the mixed gas without difficulty. The gas exhaled by the patient passes successively through the respiration face mask 5, conduit 32, exhalation tube 22 and electromagnetic valve 27, pushes the one-way valve 28 open, and is discharged out of the system. Since a load is produced on the side of the inhalation tube 20 by the action of pressure applied by the blower 17, the gas exhaled by the patient passes through the exhalation tube 22 whose interior is lower in pressure than the interior of the inhalation tube 20. In this way, the bellows 13 is contracted once for every respiration of the patient until it has the gas volume preset by the operation panel 9. As a result, the controller 2 controls the electromagnetic valves to switch the partially closed loop system into the aforementioned closed loop system. By utilizing the partially closed loop system at the initial stage for the purpose of washing in the lungs of the patient with the mixed gas of xenon and oxygen, the patient can inhale xenon of a prescribed concentration form the start of his or her inhalation and, therefore, enhancement in inspection precision can be expected.

As described above, in the xenon inhalation apparatus according to the present invention, the mixed gas prepared in the bellows 13 can be supplied to the patient in either the closed loop system or the partially closed loop system.

After completion of washing in the lungs of the patient with the mixed gas of xenon and oxygen in either the closed loop system or the partially closed loop system, the mode is changed into a respiration mode in which respiration of the patient is effected in the closed loop system. Upon change into the aforementioned respiration mode, the operation panel 9 having preset the concentrations of xenon and oxygen can be effectively used.

Particularly in the case of washing in the lungs of the patient with the mixed gas of xenon and oxygen in the closed loop system, the xenon concentration is decreased, whereas the oxygen concentration is increased. Therefore, at the time the mode has been changed into the aforementioned respiration mode, the xenon concentration is lower than that preset by the operation panel 9. For this reason, the controller 2 sends a control signal to the electromagnetic valve 41. As a result, the electromagnetic valve 41 is opened to supply xenon from the xenon-supplying means 36 into the bellows 13. However, since xenon is expensive, it is determined in view of both the xenon gas concentration and the gas volume of the bellows 13 whether the xenon should be additionally supplied into the bellows 13.

To be specific, assuming that the volume of the mixed gas preset by the operation panel 9 is 5 l and that the volume of the mixed gas still remaining in the bellows 13 after the inhalation of the patient is 2 l, for example, only when the volume of the mixed gas within the bellows 13 detected by the gas volume managing means 14 falls within 5 l preset by the operation panel 9 and when the concentration of the xenon indicated on the xenon/oxygen measuring device 38 is lower than that preset by the operation panel 9, the controller 2 causes the electromagnetic valve 41 to be opened. Therefore, if the volume of the mixed gas within the bellows 13 detected by the gas volume managing means 14 exceeds 5 l preset by the operation panel 9, the control signal for opening the electromagnetic valve 41 is not transmitted by the controller 2 to the electromagnetic valve 41 even though the xenon concentration indicated on the xenon/oxygen concentration measuring device 38 is lower than that preset by the operation panel 9. Wasteful consumption of the expensive xenon can thus be prevented. When it is required to add xenon to the mixed gas within the bellows 13, xenon in a volume of 3 l obtained by deducting the volume of 2 l of the mixed gas still remaining in the bellows 13 after the patient's inhalation from the volume of 5 l of the mixed gas preset by the operation panel 9 is supplied at one time from the xenon-supplying means 36 into the bellows 13. When the volume of the mixed gas within the bellows 13 has reached 5 l, the electromagnetic valve 41 is immediately closed. Since oxygen has been prepared in advance within the bellows 13 at the time of the one-time addition of xenon in a concentration higher than the value preset by the operation panel 9 in view of the aforementioned dead volume, it is reduced in concentration by the patient's exhalation to a value substantially the same as the value preset by the operation panel 9 without supplying additional oxygen into the bellows 13. On the other hand, addition of oxygen is effected when the electromagnetic value 42 is opened by a control signal issued by the controller 2 in accordance with the oxygen concentration value indicated on the xenon/oxygen concentration measuring device 38. When the oxygen concentration is coincident with that preset by the operation panel 9, the electromagnetic valve 42 is closed by the controller 2. In this way, the concentrations of xenon and oxygen within the bellows 13 are maintained constant, hunting due to the alternate addition of xenon and oxygen is prevented, and wasteful consumption of xenon is avoided.

The internal pressure of the inhalation and exhalation tubes 20 and 22 is detected by the pressure sensor 37. When the internal pressure is decreased and increased to such an extent that the patient breaths with difficulty, the controller 2 causes the electromagnetic valves 24 and 27 to be opened to form a gas flow passage allowing the indoor air to be introduced into the inhalation tube 20 through the one-way valve 25 and electromagnetic valve 24 and also allowing the gas exhaled by the patient to be discharged into a room through the electromagnetic valve 27 and one-way valve 28. In addition to this safety mechanism, there is provided the mechanical safety valve 26 through which the patient can respire. Thus, the xenon inhalation apparatus of the present invention has adopted a dual safety mechanism.

As has been described in the foregoing, according to the present invention, a mixed gas of xenon and oxygen can be supplied in a desired amount and desired concentrations to the lungs of a patient by the action of the blower as if mechanical one-way valves were provided in the vicinity of the respiration face mask. In the xenon inhalation apparatus of the present invention, since gas is managed in view of both the concentration and the volume thereof, any mixed gas of xenon and oxygen can be prepared within the bellows and wasteful consumption of expensive xenon can be eliminated. Furthermore, the step of washing in the lungs of a patient with the mixed gas of xenon and oxygen can be taken either in the closed loop system or in the partially closed loop system. When the closed loop system is selected, since xenon is not discharged out of the system and can therefore be utilized effectively and, at this time, fundamental data high in precision can be obtained from the xenon concentration measuring device utilizing radiation, there can be obtained effects substantially the same as those obtained in the partially closed loop system capable of introducing xenon in a given amount into the lungs of a patient from the beginning.

The xenon-supplying means has a construction such that xenon can be supplied by using disposable low-pressure xenon cylinders which have a function distinguishable from different gas cylinders. Therefore, it is unnecessary to rely on those skilled in handling high-pressure gas. Anyone can safely handle the xenon cylinders and displace the same with new ones with ease. Furthermore, the xenon cylinder once consumed is preferentially used until it is completely emptied and thereafter a new gas cylinder filled with xenon is used. Thus, it is possible to make the most economical use of xenon.

While the present invention has been described with reference to the foregoing embodiments, various changes and modifications may be made thereto which fall within the scope of the appended claims.

What is claimed is:

1. A diagnostic gas inhalation apparatus for introducing a mixed gas of a diagnostic gas and oxygen into the lungs of a patient, which apparatus comprises:

a respiration face mask for introducing the mixed gas into the lungs of a patient;

a mixed gas circulating system having a variable volume chamber having an exhalation port and an inhalation port and which is for holding a volume of mixed gas therein, and conduit means including an inhalation and exhalation tube extending in a loop between said exhalation port and said inhalation port, and a respiration tube branched from said inhalation and exhalation tube and extending to said respiration face mask, said inhalation and exhalation tube being free of check valves;

gas flow rate control means connected to said conduit means for controlling the flow rate of the mixed gas in the inhalation and exhalation tube, said gas flow rate control means including a blower connected in said inhalation and exhalation tube between said respiration tube and said inhalation port for flowing gas toward said inhalation port, and gas flow sensors connected to said inhalation and exhalation tube at positions immediately upstream and downstream of said respiration tube for sensing gas flow through said inhalation and exhalation tube in response to respiration of the patient and connected to said blower for controlling the speed of said blower for maintaining flow in said inhalation and exhalation tube in response to the sensed flows in a direction from said exhalation port to said inhalation port;

diagnostic gas concentration detecting means connected to said respiration face mask for detecting the concentration of diagnostic gas in the gas flowing into said respiration face mask;

diagnostic gas supplying means for supplying diagnostic gas into said mixed gas circulating system; and oxygen supplying means for supplying oxygen into said mixed gas circulating system.

2. A diagnostic gas inhalation apparatus as claimed in claim 1 in which said diagnostic gas supplying means comprises means for supplying xenon gas.

3. A diagnostic gas inhalation apparatus as claimed in claim 1 in which said conduit means further has a pressure relief check valve means opening from said conduit means to the ambient atmosphere and including a check valve for permitting gas flow only into said conduit means and a check valve for permitting gas flow only out of said conduit means.

4. A diagnostic gas inhalation apparatus as claimed in claim 1 in which said conduit means further has an air mixing valve means connected to said inhalation and exhalation tube at a position between the position of said gas sensors and said relief valve means and the position of said inhalation port and said exhalation port and including a first air mixing control valve and air mixing check valve permitting flow only into said conduit means and positioned upstream of said respiration tube, a second air mixing control valve and air mixing check valve permitting flow only out of said conduit means and positioned downstream of said respiration tube.

5. A diagnostic gas inhalation apparatus as claimed in claim 4 further comprising a pressure sensing means connected to said inhalation and exhalation tube downstream of said respiration tube and between said respiration tube and said second air mixing control valve and air mixing check valve for sensing pressure in said inhalation and exhalation tube, and connected to said first and second air mixing control valves for opening said valves when there is a sudden increase or decrease in pressure in said conduit means.

6. A diagnostic gas inhalation apparatus as claimed in claim 4 in which said conduit means further has first and second flow control valves in said inhalation and exhalation tube respectively upstream and downstream of the positions of said first and second air mixing control valves, a bypass connected across said loop respectively upstream and downstream of the positions of said flow control valves, and a bypass control valve in said bypass.

7. A diagnostic gas inhalation apparatus as claimed in claim 1 in which said variable volume chamber is a bellows into the inside of which said exhalation and inhalation ports open, and further comprising bellows setting means connected to said bellows for indicating the expansion or contraction of said bellows to an initial operating position for establishing an initial volume of said bellows, and gas mixing means connected to said bellows and to said bellows setting means for mixing the diagnostic gas and oxygen in a desired proportion and supplying it to said bellows and for discontinuing the supply when said bellows setting means indicates that the bellows are set to accomodate a desired volume of the mixed gas.

8. A diagnostic gas inhalation apparatus as claimed in claim 7 in which said bellows setting means comprises an endless chain attached to said bellows, a pair of rotatable gears around which said chain runs, and a potentiometer driven in response to movement of said chain for indicating the extent of movement of said chain and for outputting a signal corresponding to such movement to said gas mixing means when said bellows reaches the desired position.

9. A diagnostic gas inhalation apparatus as claimed in claim 1 wherein said diagnostic gas concentration detecting means is a xenon concentration detecting means and comprises a chamber having a mixed gas flow inlet pipe connected to said respiration face mask and a mixed gas flow outlet pipe which communicates with said conduit means, radiation generating means for irradiating the mixed gas within said chamber, a radiation detector disposed in spaced opposed relation to said radiation generating means at a predetermined distance therefrom and having an energy discriminating function for detecting the radiation emitted by the irradiated mixed gas, and concentration display means for converting the detected radiation and displaying it as a concentration of the xenon in the gas being sampled.

10. A diagnostic gas inhalation apparatus as claimed in claim 1 in which said diagnostic gas supply means comprises at least one disposable low pressure gas cylinder and said gas cylinder is provided at a nozzle portion thereof with a safety ring for distinguishing said gas cylinder from gas cylinders having no safety ring and having a gas outlet having a switch mechanism which is actuated when said gas cylinder is placed in position to bring said safety ring into contact with said switch mechanism, said switch mechanism having a movable pin moved through a prescribed amount of movement when said pin engages said safety ring, whereby diagnostic gas can be supplied from said gas cylinder and it is easy to handle the diagnostic gas.

11. A diagnostic gas inhalation apparatus as claimed in claim 10 wherein said diagnostic gas supplying means comprises at least two said disposable low pressure gas cylinders, electromagnetic valves provided one for each of said gas cylinders, pressure sensors one for each of said gas cylinders for detecting the gas pressure in the respective cylinders, and a control device connected to said pressure sensors and to said electromagnetic valves for switching over the gas being supplied from one cylinder to the other when the gas pressure in the one cylinder is detected as falling below a predetermined pressure.

* * * * *